US00PP36570P2

(12) United States Plant Patent
Williams

(10) Patent No.: US PP36,570 P2
(45) Date of Patent: Mar. 25, 2025

(54) ***COLOCASIA* PLANT NAMED 'FLOCOLEGY'**

(50) Latin Name: ***Colocasia esculenta* (L.) Schott**
Varietal Denomination: FLOCOLEGY

(71) Applicant: Brian's Botanicals, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 0 days.

(21) Appl. No.: 18/831,294

(22) Filed: Oct. 18, 2024

(30) Foreign Application Priority Data

Oct. 18, 2024 (QZ) ..... PBR 2023/2200

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

'FLOCOLEGY' is a distinctive *Colocasia* plant which is characterized by the combination of dark red foliage with prominent red-purple veins, strongly convex and recurved laminas, bright green petioles, and the stability of all characteristics from generation to generation.

2 Drawing Sheets

Latin name of the genus and species: The Latin name of the genus and species of the novel variety disclosed herein is *Colocasia esculenta* (L.) Schott.

Variety denomination: The inventive variety of *Colocasia* disclosed herein has been given the variety denomination 'FLOCOLEGY'.

CROSS REFERENCE TO RELATED APPLICATIONS

This application claims priority to the Community Plant Variety Rights application number 2023/2200, filed Oct. 18, 2023, which is herein incorporated by reference.

BACKGROUND OF THE INVENTION

Parentage: The claimed plant originated as a seedling selection, resulting from the controlled pollination of an unnamed *Colocasia esculenta* seed parent (not patented) with a second unnamed *Colocasia esculenta* plant (not patented), the pollen parent. Both parents were developed and owned by the inventor and were never commercially released. The seed parent exhibits near-black foliar veins while the pollen parent exhibits dark red foliar veins. The cross was performed by the inventor at a commercial greenhouse in Louisville, Kentucky in the summer of 2016. Seeds from said cross were harvested and germinated, and the resulting seedlings were grown to a mature size to evaluate each progeny for desirable commercial characteristics. In August of 2018, the inventor first observed one such plant that exhibited uniquely colored mid-green foliage with dark red veins and strongly recurved leaf margins. Upon confirmation of distinctness and stability of these characteristics, 'FLOCOLEGY' was selected for commercialization in August of 2021.

Asexual Reproduction: Asexual reproduction of 'FLOCOLEGY', by way of meristematic tissue culture, was first initiated in April of 2023 at a plant tissue culture laboratory in Nootdorp, The Netherlands. Through several subsequent generations of propagation there have been more than one thousand progenies produced which all maintain the unique features of the new plant.

SUMMARY OF THE INVENTION

The cultivar 'FLOCOLEGY' has not been observed under all possible environmental conditions. The phenotype may vary somewhat with variations in environment such as temperature, water availability, and light intensity, without, however, any variance in genotype. The following traits have been repeatedly observed and are determined to be the unique characteristics of 'FLOCOLEGY'. These characteristics in combination distinguish 'FLOCOLEGY' as a new and distinct *Colocasia* cultivar:

1. *Colocasia* 'FLOCOLEGY' exhibits improved cold hardiness; and
2. *Colocasia* 'FLOCOLEGY' exhibits a compact, densely-foliage growth habit; and
3. *Colocasia* 'FLOCOLEGY' exhibits dark green laminas with prominent dark red- purple veins that are borne on long bright green petioles; and
4. *Colocasia* 'FLOCOLEGY' exhibits strongly recurved foliage.

BOTANICAL DESCRIPTION OF THE PLANT

Figure 1:
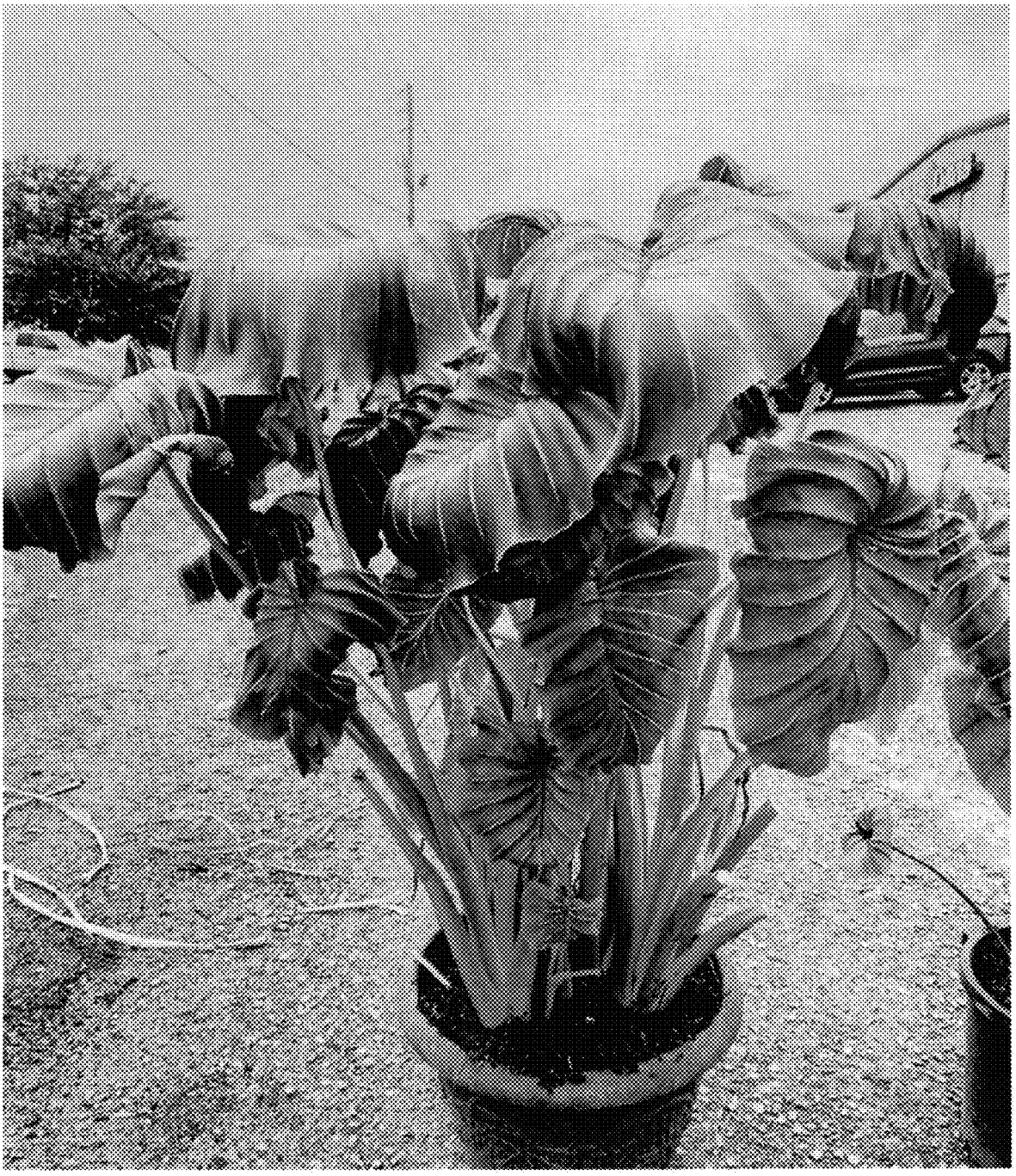
FIG. 1 illustrates, as nearly true as it is reasonably possible to make the same in color photographs of this type, an exemplary mature 'FLOCOLEGY' plant grown in a commercial greenhouse in Louisville, Kentucky.
Figure 2:
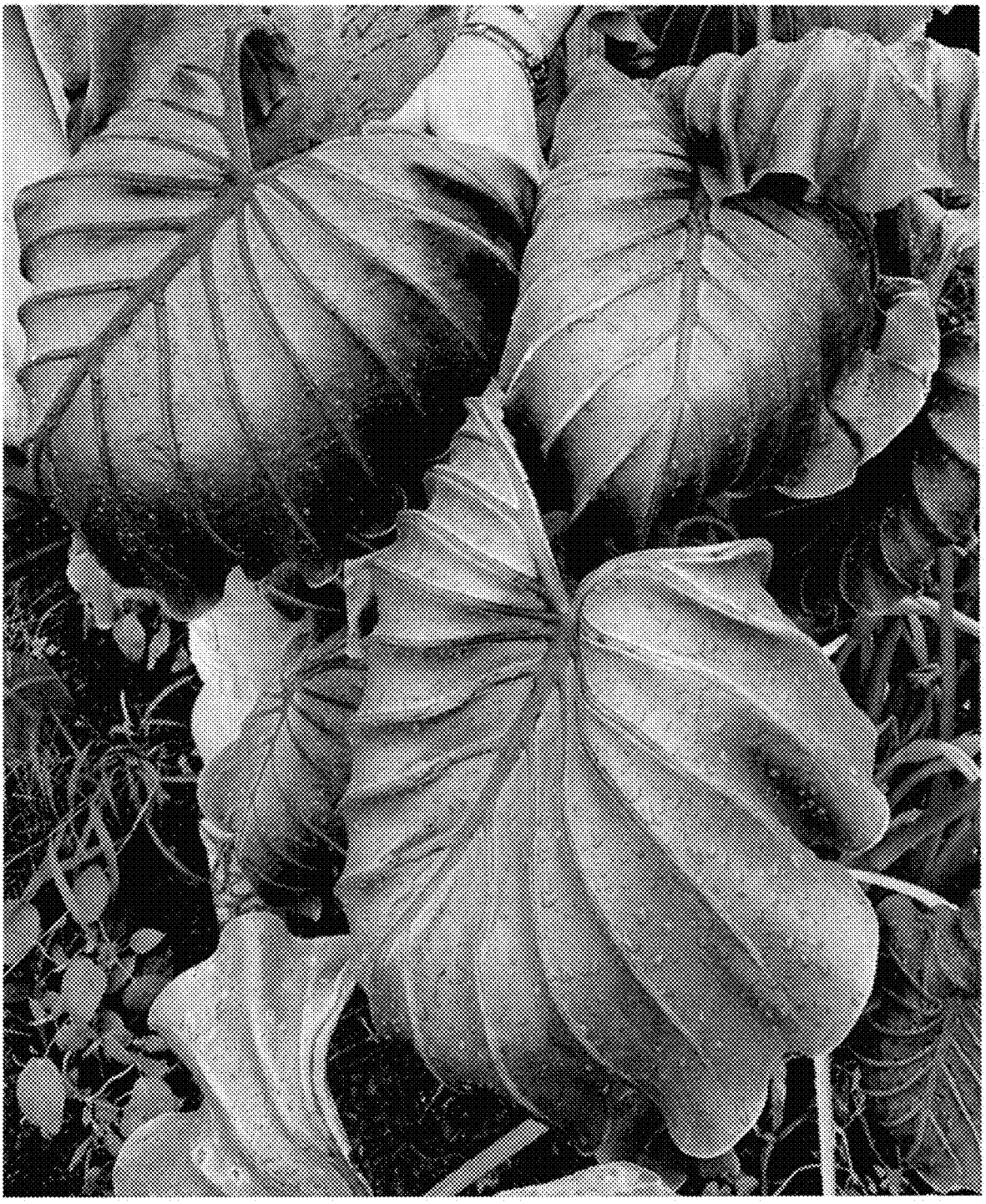
FIG. 2 illustrates, as nearly true as it is reasonably possible to make the same in color photographs of this type, the typical mature foliage of 'FLOCOLEGY'.

The following observations and measurements made in October of 2024 describe the approximations of a 'FLOCOLEGY' plant grown in a 25 cm nursery container at a greenhouse in South Carolina; United States. The plant was produced in a climate-controlled greenhouse with 35 percent shade covering and was maintained with regular overhead irrigation, slow-release granular fertilizer with a complete analysis, curative chemical pest control measures to control aphids and spider mites, and preventative fungicide applications.

Those skilled in the art will appreciate that certain characteristics will vary with older or, conversely, with younger plants. 'FLOCOLEGY' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Second Edition.

A botanical description of 'FLOCOLEGY' and comparisons with the parent plants and most similar commercial comparator are provided below.

General plant description:

*Growth habit*.—Clumping herbaceous perennial; acaulescent, with foliage arising directly from the base of each clump.

*Plant growth habit profile*.—Vase-shaped.

*Height*.—Approximately 185 cm.

*Width*.—Average 125 cm.

*Growth rate*.—Moderately fast-growing.

*Plant vigor*.—Moderately to highly vigorous.

*Propagation*.—Method — Meristematic tissue culture. Time to initiate roots — Approximately 2 to 5 weeks to initiate roots at an average ambient temperature of 29.4 degrees Celsius. Crop time — Approximately 3 to 5 weeks to produce a well-rooted, marketable 10 cm container from a rooted cutting.

*Environmental tolerances*.—Moderately high tolerance to rain; moderate tolerance to wind; not drought tolerant; tolerant of temperatures to at least 40 degrees Celsius. Cold hardy to USDA Hardiness Zone 8.

*Pest resistance and susceptibility*.—Plants have not been observed to be any more or less susceptible or resistant to pathogens and pests common to *Colocasia* sp.

Root system:

*General*.—*Colocasia* sp. exhibits a shallow root system with fleshy adventitious roots arising from large corms.

*Branching*.—Freely branched.

*Density*.—Moderately dense.

*Distribution*.—Relatively shallow.

*Texture*.—Fleshy; smooth; lacking root hairs.

Stems:

*Branching characteristics*.—*Colocasia* sp. is acaulescent; not stems or lateral branches are produced.

Foliage:

*Arrangement*.—Basal foliage is alternate to spiraled.

*Division*.—Simple.

*Attachment*.—Petiolate; peltate.

*Quantity of leaves per shoot*.—12.

*Lamina*.—Shape — Narrowly cordate. Apex — Acuminate. Base — Cordate. Aspect — Concave within the margins folding convexly along the margins. Attitude — Leaves emerge in the same plane as the petiole yet mature to oblique or pendulous. Dimensions — Approximately 80.0 cm long and 50.0 cm wide at maturity. Margin — Entire; strongly undulated. Texture and luster, adaxial surface — Strongly rugose, glabrous, and moderately glossy with a slightly iridescent quality. Texture and luster, abaxial surface — Strongly rugose, glabrous, and matte to slightly glossy. Juvenile color, adaxial surface — Green, a combination of RHS 139A and 141A; margins are suffused with green, nearest to RHS 143B. Juvenile color, abaxial surface — Green, nearest to RHS 143B. Mature color, adaxial surface — Green, nearest to a mixture of RHS 139A, 141A, 141C, and 141D. Mature color, abaxial surface — Nearest to a mixture of green, RHS 139A, and yellow-green, RHS 144A and 147A. Venation — Vein pattern — Pinnate; venation is very prominent and is raised on the adaxial laminar surface. Vein color, adaxial surface — Depending on the age of the plant, the colors of the venation will vary. During the plant's juvenile stage, the main and lateral veins is red-purple, nearest to a combination of RHS 66B and 64B. As the venation branches out, the distal ends of the lateral venation becomes orange-red, nearest to a combination of RHS 33C and 34C; ultimately becoming yellow-green, nearest to a combination of RHS 150C, 143B, and 154C. In the mature leaves, starting at the base of the lamina, the color is a light red-purple, nearest to RHS 64B, which becomes darker towards the point of attachment, ultimately becoming a darker red-purple blend, closest to a combination of RHS 71A and 83B. Vein color, abaxial surface — During the plant's juvenile stage, the main and lateral veins are an orange-red to red color, nearest to a combination of RHS 34B and 46C. As the venation branches out, the distal ends of the lateral venation become more of an orange-red coloration, nearest to a combination of RHS 33C and 34C; ultimately becoming yellow-green, nearest to a combination of RHS 150C, 143B, and 154C. Petiole — Attachment — Sheathed. Aspect — Terete. Length — Approximately 87 cm. Width — Approximately 2.2 cm, including the petiole wings, at the proximal end and 0.4 cm at the distal end. Strength — Moderately strong. Texture — Smooth and glabrous. Luster — Matte to very slightly glossy. Color — A combination of green and yellow-green, nearest to RHS 143C and 144D. Petiole wings — General Description — Two petiole wings extend to about one-third of the length of the petiole; wings clasped. Length — Approximately 7.6 cm. Width — Approximately 1.25 cm at the base. Margins — Entire. Texture and luster — Glabrous and very slightly glossy. Color — Yellow-green, nearest to RHS 144A.

Inflorescence: *Colocasia* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: Seed production has not been observed.

COMPARISONS WITH THE PARENT PLANTS

Plants of the new cultivar 'FLOCOLEGY' differ from the seed parent, an unnamed *Colocasia esculenta* plant (not patented), in the characteristics described in Table 1 below.

TABLE 1

| Characteristic | 'FLOCOLEGY' | The seed parent |
|---|---|---|
| General coloration of the petioles. | Green. | Dark maroon. |
| General coloration of the mature foliage. | Dark green with prominent dark red-purple veins. | Darker shade of green relative to 'FLOCOLEGY' with conspicuous near-black veins |
| Foliage luster. | Moderately glossy and slightly iridescent. | Slightly glossy. |
| Foliage aspect. | Laminas become strongly convex and recurved with age. | Convex at all stages of development. |

Plants of the new cultivar 'FLOCOLEGY' differ from the pollen parent, a second unnamed *Colocasia esculenta* plant (not patented), in the characteristics described in Table 2 below.

TABLE 2

| Characteristic | 'FLOCOLEGY' | The pollen parent |
|---|---|---|
| General coloration of the petioles. | A darker shade of green relative to the pollen parent. | A lighter shade of green relative to 'FLOCOLEGY' . |

TABLE 2-continued

| Characteristic | 'FLOCOLEGY' | The pollen parent |
|---|---|---|
| General coloration of the mature foliage. | Dark green with prominent dark red-purple veins. | Green foliage with raised dark maroon to black veins extending off the foliage. |
| Foliage aspect. | Laminas become strongly convex and recurved with age. | Flat. |

COMPARISONS WITH THE CLOSEST KNOWN COMPARATOR

Plants of the new cultivar 'FLOCOLEGY' differ from the closest known commercial comparator, *Colocasia* 'COPHAMA' (U.S. Plant Pat. No. 33,772), in the following characteristics described in Table 3 below.

TABLE 3

| Characteristic | 'FLOCOLEGY' | 'COPHAMA' |
|---|---|---|
| General coloration of the mature foliage. | Dark green with prominent dark red-purple veins. | Dark green with prominent black veins. |
| General coloration of the petioles. | Green. | Near-black. |

That which is claimed is:

1. A new and distinct variety of *Colocasia* plant named 'FLOCOLEGY', substantially as described and illustrated herein.

* * * * *